United States Patent [19]

Melnick et al.

[11] 4,311,794

[45] Jan. 19, 1982

[54] DETERMINATION OF BACTERIAL GROWTH ACTIVITY AND ANTIBIOTIC SENSITIVITY BY CATALASE MEASUREMENT

[75] Inventors: Joseph L. Melnick; Craig Wallis, both of Houston, Tex.

[73] Assignee: Baylor College of Medicine, Houston, Tex.

[21] Appl. No.: 160,682

[22] Filed: Jun. 18, 1980

Related U.S. Application Data

[63] Continuation of Ser. No. 959,115, Nov. 9, 1978, abandoned, which is a continuation-in-part of Ser. No. 776,323, Mar. 10, 1977, abandoned.

[51] Int. Cl.$^3$ .............................................. C12Q 1/18
[52] U.S. Cl. ..................................................... 435/32
[58] Field of Search ...................... 435/27, 32, 33, 34, 435/35, 36, 37, 38, 39, 40, 287, 291, 299, 300, 301, 316; 422/68

[56] References Cited

U.S. PATENT DOCUMENTS

| | | | |
|---|---|---|---|
| 3,838,034 | 9/1974 | Groves | 435/27 X |
| 3,907,646 | 9/1975 | Wilkins et al. | 435/291 X |
| 3,926,732 | 12/1975 | Rosen et al. | 435/27 |
| 4,065,357 | 12/1977 | Groves | 435/27 |

Primary Examiner—Robert J. Warden
Attorney, Agent, or Firm—Fulbright & Jaworski

[57] ABSTRACT

A catalase method and apparatus are disclosed for direct measurement of bacterial growth activity in the presence and absence of antibiotics, and for the determination of antibiotic sensitivity directly from clinical specimens within one and one-half to four or five hours if the agent is a catalase producer. If not, antibiotic sensitivity is measured by light obscuration. The total bacterial counts of normal flora and artifacts in the growth medium do not affect the tests. Preferably, a transducer or other pressure-measuring technique determines the positive pressure produced by the catalytic decomposition of peroxide. Aerosolization of pathogenic organisms is avoided by combining hydrogen peroxide with a quaternary compound which kills the bacteria and at the same time frees additional catalase to yield total catalase titers which are very reproducible and accurate. The method and apparatus easily detect Staphylococcus, Pseudomonas, Proteus, *E. coli*, and other catalase-producing bacteria. The method and apparatus can be used to determine bacterial growth activity in many liquids for example, cutting oils, water used for drinking, pharmaceuticals, swimming pools, cooling towers and for other purposes as well as with body fluids both qualitatively and quantitatively.

36 Claims, 1 Drawing Figure

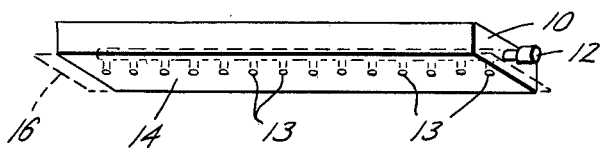

INOCULATED CULTURE TROUGH

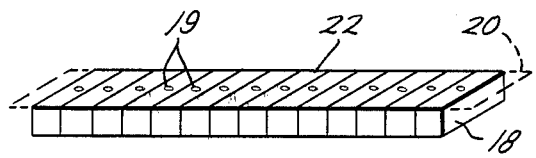

CASSETTE; 10 CELLS WITH ANTIBIOTICS, 4 CELLS WITHOUT ANTIBIOTICS

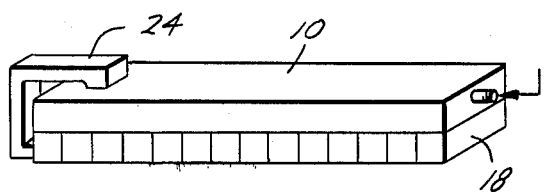

REMOVE TAPES. PUT CULTURE TROUGH ON TOP AND LOAD CASSETTE THROUGH TROUGH

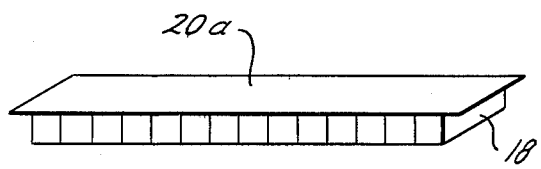

REMOVE TROUGH AND RESEAL CASSETTE

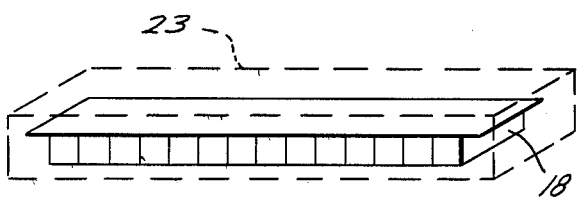

INCUBATE, OPTIONAL

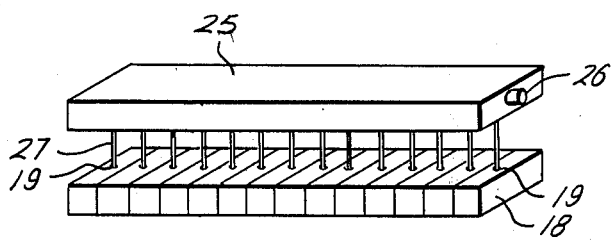

PEROXIDE WITH STERILIZING AND LYSING AGENT INJECTION INTO CELLS OF CASSETTE AND ALLOWING PRESSURE EQUALIZATION WITH THE ATMOSPHERE, DYE OPTIONAL

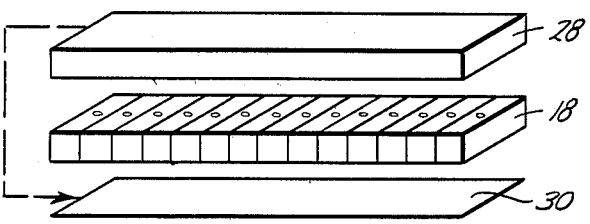

PRESSURE READ-OUT BY POSITIVE PRESSURE TRANSDUCER INCLUDING PRINT-OUT

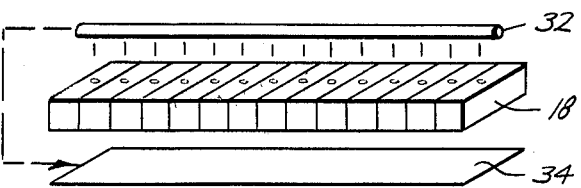

SPECTOPHOTOMETER, LIGHT OBSCURATION, READ-OUT, BACK UP

DETERMINATION OF BACTERIAL GROWTH ACTIVITY AND ANTIBIOTIC SENSITIVITY BY CATALASE MEASUREMENT

This is a continuation of application Ser. No. 959,115, filed on Nov. 9, 1978 and now abandoned. Ser. No. 959,115 is a continuation-in-part of application Ser. No. 776,323, filed on Mar. 10, 1977 and now abandoned.

BACKGROUND OF THE INVENTION

The resistance of microorganisms to antibiotics presents a serious public health problem. Extensive use of immunosuppressive drugs and broad spectrum antibiotics has not only caused a change in the antibiotic-resistance patterns of bacteria, but has also caused emergence of fungal infections. When one considers that antimicrobials are the second most highly used group of drugs, it is clear that prevention and control of infectious disease pervades virtually all forms of medicine. It has been estimated that 50% of the time antimicrobials are used, either they are given unnecessarily or the wrong drug or dose is used. In addition, early administration of the appropriate antibiotic greatly improves the chances for survival of the patient. Therefore, it is highly desirable for an inexpensive, effective and rapid method and means to be made available to the clinician and laboratory diagnostician for determination of antibiotic sensitivity.

CURRENT STATE OF THE ART

Antibiotic sensitivity of pathogenic organisms has been, and is presently, determined by the methods described:

(1) Tube dilution or Minimum Inhibiting Concentration (MIC). The offending organism is isolated from a colony on agar medium. It is grown in broth in pure culture, and is then serially diluted to contain different viable concentrations in the presence of different antibiotics and different concentrations of each antibiotic. Tubes are then allowed to incubate overnight at 37° C. and the lowest dilution of antibiotic that prevents growth of the organism is considered the antibiotic of choice and dosage determined accordingly. However, when one considers that it may be necessary to run 10 antibiotics in a single test, with each antibiotic at 5 levels, and the organism challenged at viable counts of $10^3$, $10^4$, $10^5$ and $10^6$, a single test can be exceedingly expensive and cumbersome. This practice of tube dilution is not routinely used and costwise is prohibitive.

(2) Diffusion. Bauer et al. (Bauer, A W, Kirby, W. M. M., Sherris, J. C., and Turck, M., Am, J. Clin. Path. 45:493, 1964) standardized the diffusion test for antibiotic sensitivity that has gained wide acceptance. This method consists of, first, isolation of the pathogen in the form of a colony with requires about 18-36 hours to form on agar. The colony is then suspended in medium, and when in log phase growth, which requires an additional 3-5 hours, a heavy seed is spread over an agar plate. Antibiotic discs are then placed on top of the bacterial lawn, and after an additional 5-18 hours' incubation, zones of inhibition are scored and the antibiotic of choice determined by the largest zone of inhibition. This has proven to be a useful approach to antibiotic sensitivity determinations, but it is time-consuming and requires skilled technicians trained in bacteriology.

(3) Automated or Semi-Automated Antibiotic Sensitivity Systems. Pfizer, Abbott Laboratories, Fisher Scientific and other companies are presently providing systems for automated or semi-automated determinations of antibiotic sensitivities. In these cases, the pathogen again must first be isolated in the form of a colony. The colony is then suspended in broth so that turbidity is manifest. The seeded broth is placed into cassette cells, each containing a different antibiotic. Then the cassette is monitored in a light-scattering device which indicates increases in bacterial numbers. The antibiotic of choice is determined after 4-8 hours; it is the antibiotic present in the cell that registers the least increase in bacterial numbers as measured by light scattering. There are many precautions associated with this technology, which are readily admitted by each of the manufacturers.

Organisms such as Staphylococcus are not easily examined in these instruments, since they tend to aggregate, which affects the light scattering measurement devices and gives false values.

Slime-producing agents, such as Pseudomonas, and pellicle-producing agents also affect the efficiency of these systems to determine antibiotic sensitivities.

The seed used in these instruments is derived from a bacterial colony that contains large numbers of dead bacteria which may lyse soon after they are added to the instruments. Thus the values scored by the instruments may indicate a decline in bacterial numbers within the first 1-3 hours, which affects the test.

Further, it is sometimes difficult to accurately measure bacterial numbers using a tiny beam which only evaluates a very small fraction of the bacterial population under test.

Automated and semi-automated antibiotic sensitivity systems have been marketed for the past five years, but none has had the desired success. The basic reason for their failure to win over the microbiological marketplace has been that the units do not readily determine the antibiotic sensitivity of organisms such as Pseudomonas, Staphylococcus, Proteus and *E. coli* —agents which probably cause 90% of infectious disease problems. They cannot efficiently evaluate these organisms because the units use light-scattering techniques for their determinations, and pellicle formation, aggregation and slime formation interfere with the optic measurements. In addition, cost is often prohibitive, with units ranging from $25,000 to $50,000 and over. Thus, there is a need in the marketplace for a method and unit that overcome the problems which are manifest with the units now available on the market and require considerably reduced investment capital to provide a manual, automated or semi-automated antibiotic sensitivity analysis. For a review of the history of automated microbiology, reference is made to an article in the May 26, 1976, issue of "Bio-Insight".

Also, there has been considerable difficulty and expense in measuring bacterial growth activity in water used for drinking, pharmaceuticals, swimming pools, cooling towers as well as other fluids containing water, such as cutting oils, which bacterial growth poses real problems and expense in keeping bacterial counts at acceptable levels.

Surprisingly, we found that antibiotic sensitivity could be accurately determined by measuring a bacteria-synthesized product rather than assaying bacterial numbers. Bacterial catalase, which is present in all aerobic bacteria, was unexpectedly found to be the product of choice. A search of the literature failed to provide any efficient method for measuring bacterial catalase, since all workers who had attempted quantitatively to measure catalase by breakdown of hydrogen peroxide indicated the irreproducibility of their methods. When we exposed bacteria containing catalase to hydrogen peroxide in sealed tubes, we also failed to obtain linear values when different amounts of bacteria were used. We also failed to obtain similar results from duplicate tubes.

However, we unexpectedly discovered that there were four parameters required to obtain efficient and reproducible results in the measurement of bacterial catalase with peroxide:

(1) The concentration of peroxide was critical, and thus we found that a final concentration of 1% peroxide in the bacterial culture was required (the final reaction product), with an allowable variation between 0.1% and 2.25%, but 1% being optimum.

(2) The reaction of bacterial catalase and peroxide in a sealed tube or cell required that the freshly released $O_2$ (breakdown of $H_2O_2$ to water and $O_2$ by the catalase) had to be forced from the aqueous phase to be accurately detected, and thus by manual shaking of the tube or sonication, accurate and reproducible values could be measured on instruments used for the measurement of positive pressure.

(3) The reaction between the bacterial catalase and peroxide in a sealed tube required adequate time to form $O_2$ in order to reproducibly measure freshly formed gas. We found that a 15-minute reaction between the reactants (catalase and peroxide) was critical, with time limits between 10 minutes and 30 minutes, with 15 minutes being ideal.

(4) Finally, in order to yield optimal sensitivity, the air space to aqueous volume ratio in sealed tubes was found critical. Thus, experimentation revealed that 70-90% of the tube, cell or other vessel should contain the bacterial culture and peroxide, and the void space should be between 10-30% to offer the highest sensitivity for detection of small amounts of released $O_2$.

(5) Another feature of the invention is the addition of a disinfectant such as a quaternary compound along with the peroxide to kill the bacteria. This prevents infectious aerosols being released to the environment and also enhances the accuracy and reproducibility of the test in that it frees additional catalase so that the total catalase is readily measured.

(6) A further feature of the invention is that a dye such as methylene blue is added together with the peroxide and Roccal so that the operator is immediately aware that the cultures have been disinfected and the cassette or tubes can be safely discarded.

In view of these unexpected findings, we discovered that great accuracy and reproducibility were achieved when (1) bacterial cultures were exposed to a final concentration of 1% peroxide, 1% Roccal and 0.01% methylene blue in a sealed tube having 25% airspace, and, (2) the cultures were then held for 15 minutes at 35°-37° C.; and (3) immediately before determining the amount of positive pressure produced by the reactants in the tube, the tube was shaken for 6 seconds, and (4) the positive pressure was then scored on either a manometer or transducer by perforating the tube stopper with a needle which led directly into the manometer or transducer. Results were obtained which were within a range of 0.01% when 10 replicate samples were tested.

Since the reaction between bacterial catalase and peroxide was not affected by aggregated bacteria, slime or pellicles or other artifacts, the antibiotic sensitivity determinations using this method offered many advantages over the previously known methods for determining bacterial cell growth and its selective inhibition by antibiotics.

Furthermore, the measurement of bacterial catalase represents the sum of the catalase molecules present in all bacteria in the tube, cell or vessel used for the test. This is a highly accurate assay system, as opposed to the light scattering devices, which only measure a tiny proportion of the total bacteria in the test system.

Similar unexpected findings were obtained in determining bacterial growth activity in water used for a variety of purposes and liquids susceptible to bacterial growth such as those containing water, such as cutting oils used in machining various parts and the like.

SUMMARY OF THE INVENTION

The present invention is directed to a method of and means for detecting bacterial growth and antibiotic sensitivity of bacteria in various liquids and also for determining antibiotic sensitivity directly from clinical specimens or from an isolated colony from agar plates, within one and one-half to four and five hours if the agent is a catalase producer. Bacteria and bacterial growth activity are detected by measuring cell-associated (bacterial) catalase, which is usually five-to-ten-fold more sensitive than the turbidimetric and/or light-scattering methods used by units currently available. The present catalase detection analysis is not affected by artifacts in the growth medium, such as bacterial aggregation, slime production, or pellicle formation, as are the units utilizing the turbidimetric and/or light-scattering methods. In addition, the present catalase analysis measures Staphylococcus, Pseudomonas, Proteus, and *E. coli* catalases efficiently, whereas the turbidimetric and/or light-scattering methods find these agents the most difficult organisms to evaluate.

The present catalase analysis preferably utilizes a variable reluctance transducer or other types of transducers to measure positive pressure produced by the catalytic decomposition of peroxide. A Transducer with a sensitivity of 0.01 psi and reproducibility within 0.05% is satisfactory. About 95% of organisms causing disease are catalase positive. (The organisms that are not measurable by catalase, which include the strict and facultative anaerobes, are measured in a backup unit by light obscuration.) The catalase method and means can be used for direct measurement of bacterial growth activity, in the present or absence of antibiotics, and for determination of antibiotic sensitivity of pathogenic bacteria and for measurement of MIC if the pathogenic organism is present to a greater titer than the natural flora, which is the usual case when pathogens are present in urine, spinal fluids, blood, or in areas of local sepsis (ear and eye infections or wounds). In other cases, isolated colonies must be obtained, after which the antibiotic sensitivity can be determined within 1 to 1½ hours. Hydrogen peroxide is combined with a quaternary compound, which together sterilize and lyse the bacteria thereby increasing catalase titers, because the total catalase is then immediately available for measurement. The quaternary compounds efficiently inactivate the bacteria when combined with the peroxide thereby avoiding the problem of aerosolization of pathogenic organisms and yet, unexpectedly, catalase titers are increased. Preferably, a small quantity of a dye is also combined with the peroxide and quaternary compounds to color the chambers in which the reaction is carried out to give a visible indication that they have been subjected to the catalase reaction.

Preferably, the quaternary compound is Roccal, which is readily available on the market, and is a solution of 1% alkyldimethylbenzyl ammonium chloride in water. Preferably, the dye is methylene blue.

Any quaternary compound can be used as well as any desired dye, as set forth later. In this connection it is noted that the quaternary compounds have no effect on hydrogen peroxide per se, that is, in the absence of bacterial catalase.

The method and apparatus are useful for detecting bacterial growth activity in liquids susceptible of bacterial growth, such as water used for drinking, pharmaceuticals, swimming pools, cooling towers, cutting oils, body fluids as well as antibiotic sensitivity and for other purposes.

It is therefore an object of the present invention to measure bacterial growth activity directly from clinical specimens quickly and inexpensively if the agent is a catalase producer.

It is a further object of the present invention to provide a method of and means for determining the antibiotic sensitivity of bacteria, if a catalase producer, quickly, inexpensively, reproducibly, and quantitatively.

It is a further object of the present invention to provide a method of and means for effectively determining the antibiotic sensitivity of bacteria, if a catalase producer, within four to five hours.

A further object of the present invention is the provision of a method of and means for determining antibiotic sensitivity by measuring bacterial catalase by positive pressure produced by the catalytic decomposition of peroxide without aerosolization of pathogenic organisms.

Yet a further object of the present invention is the provision of a method of and means for catalase detection for antibiotic sensitivity in which increase in catalase synthesis can be detected prior to multiplication of the bacteria.

A further object of the present invention is the provision of a method of and means for determining bacterial sensitivity in which the total bacterial count of normal flora in patients does not affect the results.

A further object of the present invention is a method of and means for determining antibiotic sensitivity readily and easily of organisms, e.g., Staphylococcus, Pseudomonas, Proteus and *E. coli*, difficult to determine by prior methods and systems.

A further object of the present invention is the provision of a method of and means for readily, easily and quickly determining the antibiotic sensitivity of 95% of organisms causing disease by the catalase method and system.

A further object of the present invention is the provision of a method and means for determining antibiotic sensitivity in which hydrogen peroxide is combined with a quaternary compound which kills the pathogens and frees additional catalase, which increases the catalase titers and makes them highly accurate and reproducible.

A further object of the present invention is the provision of a method and means for determining antibiotic sensitivity in which a dye is combined with hydrogen peroxide and a quaternary compound to indicate catalase reaction.

A further object of the present invention is the provision of a method and means for determining bacterial growth activity in water used for drinking, pharmaceuticals, swimming pools, cooling towers and the like, readily, easily, quickly and inexpensively.

A further object of the present invention is the provision of a method and means for determine bacterial growth activity in cutting oils and other liquids containing water, readily, easily, quickly and inexpensively.

A further object of the present invention is the provision of antibiotic sensitivity analysis which may be performed manually, semi-automatically or automatically at relatively low cost and in five hours or less.

Other and further objects, features and advantages appear throughout.

DESCRIPTION OF THE DRAWINGS

The drawing is a diagrammatic illustration of means for determining antibiotic sensitivity according to the invention and illustrating the steps of the method of the invention.

DESCRIPTION OF THE PREFERRED EMBODIMENTS

The present invention is based upon the surprising discovery that an indication of bacterial growth activity and antibiotic sensitivity can be determined by contacting a culture medium inoculated with body fluids containing a pathogenic organism or contacting a sample of liquid susceptible to bacterial growth, such as water or liquids containing water with hydrogen peroxide, a quaternary compound, and, if desired, a dye to color the treated cells. The concentration in the catalase reaction product should be from about 0.1% to 2.25% by weight peroxide, with 1% by weight being preferred, about 0.1% to 9.0% by weight quaternary compound, with 1.0% being preferred, and, if a dye is used, from about 0.1% to about 0.01% by weight dye. Under normal conditions, we have found that a solution containing from about 0.15% to about 15.0% by weight of hydrogen peroxide, and from about 0.001% to about 3% by weight of a quaternary compound, and, if a dye is used, from about 0.1% to about 0.01% by weight dye will provide these concentrations in the final reaction product. If desired, however, the peroxide, quaternary compound and dye can be added separately. For convenience, however, the solution of them is preferred. Unexpectedly, by combining a quaternary compound with hydrogen peroxide not only is aerosolization of pathogenic organisms avoided, but the quaternary compound lyses the bacteria and produces higher catalase titers providing good results.

There are four parameters required to obtain efficient and reproducible results in the measurement of bacterial catalase with peroxide. These are:

(1) The concentration of peroxide is critical, and a final concentration of peroxide in the reactant product between 0.1% and 2.55%, with 1% being optimum, is required:

(2) There is sufficient reaction time between the bacterial catalase and peroxide in a sealed tube and adequate to form $O_2$ in order to reproducibly measure freshly formed gas, with time limits between 10 minutes and 30 minutes, with 15 minutes being preferred;

(3) The reaction of bacterial catalase and peroxide in a sealed tube or cell requires that the freshly released $O_2$ (breakdown of $H_2O_2$ to water and $O_2$ by the catalase) has to be forced from the aqueous phase to be accurately detected, and thus by shaking the tube or sonication, reproducible values can be measured on instruments used for measurement of positive pressure;

(4) In order to yield optimal sensitivity, the air space to aqueous volume ratio in sealed tubes was found to be critical, experimentation revealing that 70-90% of the tube, cell or other vessel should contain the bacterial culture, peroxide, and quaternary disinfectant, and the void space should be between 10-30% to offer the highest sensitivity for liberation and detection of small amounts of released $O_2$.

The term "body fluid" containing a pathogenic organism includes urine, septic wound exudate, spinal fluid, blood culture fluid or isolated colonies from such a fluid.

The term "liquid" includes liquids in which bacteria grow, for example water and liquids containing water.

EXAMPLE 1

This example describes a new method for antibiotic sensitivity determination using the catalase method and system of the present invention.

As a model, a patient with a urinary infection is examined.

(1) A midstream urine sample is obtained. The urine is processed by the catalse method below, and thus the antibiotic sensitivity is determined 36 hours sooner than by methods requiring the formation of a colony. (As a precautionary procedure, an aliquot of the urine is plated on agar media to isolate the pathogen, in the event the pathogen does not produce catalase. However, most pathogens produce catalase.)

(2) 1-5 ml of urine is added to about 15 ml of nutrient broth prewarmed to 37° C. Since bacterial pathogens are present in patients suffering with bacteriuria in greater numbers than normal bacterial flora (about 10,000 to 1,000,000 pathogens for 1 bacterium of the normal flora), the normal flora will not offer a problem in the test.

(3) The seeded broth is then dispensed into all compartments or cells of a 14-cell cassette, 1 ml/cell. The first 4 cells of the cassette are control cells (labeled 1-4), and the remaining 10 cells contain antibiotic discs as indicated in the table below. The cassette is then stoppered.

(4) Control cell #1 is then tested to determine the baseline level of catalase present in the seeded broth at "zero" time.

(a) 0.1 ml of 10% peroxide is added to the 1 ml culture broth in cell #1 by injection of the peroxide through the rubber stopper of the cell and then the pressure produced by injection of the peroxide volume is relieved by the venting apparatus on the injector.

(b) The cassette is allowed to incubate further at 37° C. for 15 minutes, thus allowing the bacterial catalase in cell #1 to decompose the added peroxide.

(c) At the end of the 15-minute incubation period the catalase titer of this control is determined by shaking the cassette to release aqueous phase $O_2$ and perforating the rubber stopper of cell #1 with the transducer needle, which measures the amount of catalase based on splitting peroxide into water and $O_2$, and the psi is recorded. In this case the psi registered on the digital readout of the transducer system was 0.08.

(5) The cassette is then further incubated at 37° C. to allow bacterial growth to proceed. After an additional hour, cell #2 was examined as described for cell #1, using the same steps described above. The psi at 1 hour was 0.92, or an increase in pressure of slightly greater than 10-fold over cell #1, which was read at zero hour. This indicated significant synthesis of catalase, and thus the antibiotic-containing cells could now be read.

(6) Cells #5-14 containing the antibiotics were then immediately examined to determine the amount of catalase synthesized in the presence of these antibiotics. Peroxide was injected into each cell as described above, and psi values were read after 15 minutes as described above (e.g., shaking of cassette, and perforating each cell with a transducer needle). The results are shown below, with interpretation of results.

TABLE I

| Cell No. | Antibiotic (10 mcg) | psi | Interpretation |
|---|---|---|---|
| 1 | — | 0.08 | control at "0" hour |
| 2 | — | 0.92 | control at 1 hour |
| 3 | — | not used | |
| 4 | — | not used | |
| 5 | penicillin | 0.86 | resistant |
| 6 | ampicilin | 0.81 | resistant |
| 7 | streptomycin | 0.62 | resistant |
| 8 | kanamycin | 0.09 | sensitive |
| 9 | tetracycline | 0.08 | sensitive |
| 10 | gentamycin | 0.06 | sensitive |
| 11 | colistin | 0.71 | resistant |
| 12 | chloromycetin | 0.12 | intermediate |
| 13 | aureomycin | 0.84 | resistant |
| 14 | erythromycin | 0.76 | resistant |

Thus, the cells containing kanamycin, tetracycline and gentamycin after 1 hour had the same psi values as cells #1 at zero time, indicating that the bacteria present therein were not able to synthesize catalase. Thus, these early results indicate three drugs of choice. However, bacteria may require 2-4 hours in the presence of antibiotics before emergence of resistant forms. Therefore, a duplicate cassette should be run alongside the original cassette described above but for an additional 3 hours in order to determine true bactericidal effects and determine the optimal antibiotic for treatment of the patient. An added advantage of our catalase method is that catalase is a labile enzyme and will decompose at 37° C. after 2-3 hours if the bacterial cell is not biosynthetically active. The results on the duplicate cassette, in which catalase measurements were made at 4 hours, are described below.

TABLE II

| Cell No. | Antibiotic (10 mcg) | psi | Interpretation |
|---|---|---|---|
| 1 | — | 7.24 | control at 4 hours |
| 2 | — | not used | |
| 3 | — | not used | |
| 4 | — | not used | |
| 5 | penicillin | 6.96 | resistant |
| 6 | ampicillin | 6.90 | resistant |
| 7 | streptomycin | 5.42 | resistant |
| 8 | kanamycin | 0.19 | intermediate |
| 9 | tetracycline | 0.02 | sensitive |
| 10 | gentamycin | 0.01 | sensitive |
| 11 | colistin | 5.41 | resistant |
| 12 | chloromycetin | 1.46 | intermediate/resistant |
| 13 | aureomycin | 7.00 | resistant |
| 14 | erthromycin | 6.41 | resistant |

These results indicate that only tetracycline and gentamycin are bactericidal for the agent under the test since the catalase titers are lower at 4 hours, indicating decomposition of the enzyme, than the initial titer at time zero (shown in Table I). Kanamycin, which appeared to be a drug of choice at 1 hour, emerged at 4 hours as an antibiotic to which the bacteria were developing resistance. Such data could only be obtained by this catalase method, since such fine differences could not be detected by light-scattering devices.

In the event a colony had been used as a source of seed in lieu of the urine per se, the broth seeded with the colony would have been processed exactly as described above.

In the event that the organism processed above proved not to be a catalase producer, the antibiotic sensitivity would have been determine by the back-up method (light obscuration). Thus, when the urine was initially plated on agar, colonies formed the next morning would have been used to seed broth for determination of antibiotic sensitivity by light obscuration.

Referring now to the drawings, body fluids or isolated colonies are seeded into a sterile broth culture medium. The seeded culture medium is contained in individual cells or cassettes or can be introduced into a cassette by the inoculated culture trough 10 through the closable opening 12. The culture trough 10, as illustrated in the drawing, has a series of dispensers 13 at its bottom 14, which is closed or sealed by a thin layer of sterile waterproof tape 16.

A cassette 18 is provided which has the same number of cells with the openings 19 as in the culture trough which is covered by a thin layer of sterile waterproof tape 20 which seals the openings 19. In the embodiment illustrated in the drawing, the dispensers 13 are 4 mm in diameter which match the openings 19 in the cassette 30 and each cell of the cassette 18 has a 2-ml capacity. In the form of the invention illustrated in the drawing, 10 of the cells contain antibiotics whose sensitivity is to be determined and four cells are controls without antibiotics. Cassettes may be provided with a variety of antibiotics as well as different concentrations of antibiotics. Preferably, the cassette 18 is made of plexiglass and is of good optical quality. The upper surface 22 of the cassette 18 preferably has a thin cover of plexiglass and the openings 19, in the form illustrated, are 7.5-mm and disposed in the center of each cell for receiving the matched dispensers 13 in the inoculated culture trough 10.

In loading the cassette 18 with inoculated or seeded culture, the tapes 16 and 20 are removed, the inoculated culture trough 10 is then placed on top of the cassette 18 with the dispensers 13 in alignment with the openings 19 and clamped together by the clamp diagrammatically illustrated at 24. Preferably, the removal of the tapes 16 and 20 and placing of the culture trough 10 on the cassette 18 should be done under a hood so that aseptic assembly is practical.

The cap is removed and the seeded broth samples are loaded into each of the cells of the cassette 18 by introduction into culture trough 10 through the opening 12. The culture trough 10 is then removed from the cassette and discarded and the cassette is then resealed with sterile tape 20a, preferably while still under a hood.

Preferably, the loaded and resealed cassette 18 is inverted for several minutes to elute all of the antibiotics in the individual cells and then reinverted. Optimally, if desired, the cassette 18 may then be placed in an incubator for a period of time, 30 minutes being typical, but it can be longer depending on the culture and growth.

A dispenser 25 is provided having the needle-like spouts 26 which are in alignment with the openings 19 in each of the cells of the cassette 18. The dispenser 25 has a closable opening 26 for loading into it a mixture of hydrogen peroxide and a sterilizing and lysing agent, with or without a dye, as described in more detail later herein. While a single loading opening 26 is shown for the dispenser 25, in practice the dispenser 25 is so constructed and arranged as to be able to load one or more of the cells of the cassette 18 or all of them at one time, as desired.

The cassettes may be of any desired shape, rectangular as shown, circular, or the like, and may be formed of any suitable material. Preferably, the cells are formed of a transparent material, such as plexiglas having good optical quality, so that a light obscuration read-out can be used as a back-up in the event the agent is not a catalase producer. No detailed description of the incubator 23, the transducer 28 and the light obscuration system indicated as 32 and 34 is given or deemed necessary as these are all conventional, there are many available on the open market, and any of them can be used.

The catalase-transducer unit can be operated manually, semi-automatically or completely automatically.

Any of the aniline dyes, such as methylene blue and toluidine blue, can be used. Methylene blue is presently preferred in view of its wide availability and low cost.

Any of the quaternary compounds can be used as a sterilizing and lysing agent, for example: Roccal (alkyldimethylbenzyl ammonium chloride), Cetrimide (cetyltrimethylammonium bromide), Ceepryn (cetylpyridinium bromide or chloride), Fixanol (tetradecylpyridinium bromide), Emulsept [N-(acylcollaminoformylmethyl) pyridinium chloride], cetramide (a mixture of $C_{12}$, $C_{14}$, $C_{16}$ alkyl trimethylammonium bromide), Arquad S (alkyltrimethylammonium chloride), Bradosol (phenoxythyldimethyldodecylammonium bromide), Virac [acylcholaminoformylpyridinium chloride complexed with iodide (an iodophor)], Laurodine (4 aminoquinalidiniumlauryl acetate), or Triburon (-iononetric lobisonium chloride).

One of the appealing aspects of using catalase detection for antibiotic sensitivity is the fact that increase in catalase synthesis can be detected prior to multiplication of the bacteria. This would be expected, of course, in view of the nature of bacterial physiology and the process of multiplication.

In the following description, Tables III–VI, and Examples 2–4, the mixture of 10% hydrogen peroxide, 0.1% Roccal and 0.01% methylene blue, by weight, were used, although other concentrations, other quaternary compounds and dyes can be used as set forth herein.

A base line reading is then taken of one of the control cells by the variable reluctance transducer 28. After about a fifteen minute wait, the transducer 28 is again activated and a reading of the control cell is made. The reading can be made on a digital display, and, if desired, imprinted on the front of the cassette at the base of the cell. After fifteen minutes, or sooner, another pressure reading is taken by the variable pressure transducer 28 and what is read is a difference between the pressure immediately after the reagent injection and the time of the pressure reading. If the pressure indicates adequate growth, as later described, then the antibiotic sensitivity test can proceed; otherwise, the operator will wait some time for further growth, for example, about one hour, and take a pressure reading on cell no. 2 as upon cell no. 1. If there is inadequate pressure for cell no. 2, the test will be continued as a light obscuration test. If pressure, which is indicative of catalase growth, is adequate in a control cell, then the test can proceed by measurement of catalase production in the presence of the antibiotics.

At this time, all of the cells of the cassette 18 are filled with the reagents and, after fifteen minutes, pressures are read by the variable reluctance transducer 28 and are displayed for each cell by the transducer, not shown. These numbers can be copied down by the operator, or automatically transferred to a print-out 30 by a printer.

Assuming that the clinician will want MIC data or more positive data to indicate that the antibiotic is bactericidal and not bacteriostatic, double-cassette units are used, and a 50-ml culture trough will be used as described above.

The cells are again read at 2.5 hours. A typical read-out with evaluation is set forth in Table III below for a strain of Pseudomonas. The read-out prints the psi scored by the transducer, and the interpretation of the read-out.

TABLE III

| Cassette cell no. | Time read (hrs) | psi | Results |
|---|---|---|---|
| C1 | 0 | 0.08 | — |
| C2 | 2.5 | 0.82 | — |
| C3 | | | |
| C4 | | | |
| Erythromycin | 2.5 | 0.79 | R |
| Ampicillin | 2.5 | 0.81 | R |
| Penicillin | 2.5 | 0.75 | R |
| Carbencillin | 2.5 | 0.45 | R |
| Tetracycline | 2.5 | 0.06 | S |
| Cephalothin | 2.5 | 0.73 | R |
| Gentamycin | 2.5 | 0.04 | S |
| Colistin | 2.5 | 0.04 | S |
| Kanamycin | 2.5 | 0.76 | R |
| Chloramphenicol | 2.5 | 0.09 | S |

After the cells are read at 2.5 hours, the duplicate cassette 18 is returned to the incubator 23 or simply held for an additional 2.5 hours, and at that time a total read-out is made again. A typical example is given in Table IV below using the same read-out and organisms as set forth in Table III.

TABLE IV

| Cassette cell no. | Time read (hr) | psi | Results | Time read (hr) | psi | Results |
|---|---|---|---|---|---|---|
| C1 | 0 | 0.08 | — | | | |
| C2 | 2.5 | 0.82 | — | | | |
| C3 | | | | 5.0 | 6.24 | — |
| C4 | | | | | | |
| Erythromycin | 2.5 | 0.79 | R | 5.0 | 6.15 | R |
| Ampicillin | 2.5 | 0.81 | R | 5.0 | 6.22 | R |
| Penicillin | 2.5 | 0.75 | R | 5.0 | 6.04 | R |
| Carbencillin | 2.5 | 0.45 | R | 5.0 | 5.41 | R |
| Tetracycline | 2.5 | 0.06 | S | 5.0 | 0.00 | S |
| Cephalothin | 2.5 | 0.73 | R | 5.0 | 6.00 | R |
| Gentamycin | 2.5 | 0.04 | S | 5.0 | 0.00 | S |
| Colistin | 2.5 | 0.04 | S | 5.0 | 0.00 | S |
| Kanamycin | 2.5 | 0.76 | R | 5.0 | 6.20 | R |
| Chloramphenicol | 2.5 | 0.09 | S | 5.0 | 0.19 | I |

As set forth above, very subtle differences in antibiotic sensitivity can be determined by the transducer measurement of catalase. At 2.5 hours, four antibiotics indicated sensitivity (S). However, at 5.0 hours, Chloramphenicol increased in psi to 0.19, indicating minimal but significant synthesis of catalase by the bacteria in the presence of this antibiotic.

If desired, MIC cassettes can be provided with two antibiotics in different concentrations so that the alignment of the cassette consists of four control cells and five cells with an antibiotic of choice with levels of antibiotics at 0.1, 0.3, 1.0, 3.0, or 10.0 $\mu$g/ml or any other concentration required or desired. The following five cells contain a second antibiotic of choice with a similar concentration of drug.

In the event a dual cassette is not desired, selected antibiotics can be used in duplicate so that the first four cells are still control cells, the next five cells contain different antibiotics, and the following five cells are replicates containing the same antibiotics, either at the same or at different concentrations. Read-outs can then be made in duplicated by adjusting the total read-out to read only the control cell and the first five antibiotic cells. By readjustment of the total read-out control center for later readings, the transducer can read a control cell and the last five antibiotic cells can give a total read-out if the antibiotic cells are all to be read at the same time.

When the read-outs made at either 2.5 or 5.0 hours are negative or the same as the base line read-out, the cassette 18 is transferred to a spectrophotometer, here illustrated diagrammatically as a light source 32 and a read-out 34. The cassette 18, which is made of a transparent material, preferably plexiglas, is subjected to light obscuration measurement and the read-out is adjusted to 0.00, recordings are made of all the cells and the total read-out 34 indicates ight obscuration and gives results as to sensitivity, insensitivity or resistance of the antibiotic under investigation.

By reactivating the scanning device, the spectrophotometer will initiate a second cycle and read the control cell until 1.5 relative light obscruation units are recorded on the read-out, display, and a second reading can then be taken. This phase can be repeated as often as required and each additional activation will increase the light obscuration 1.500 units over the previous reading so that accurate results may be obtained.

It is noteworthy that light obscuration measurements will be available 2–8 hours later than catalase assays if the agent is a catalase produced. Thus, the spectrophotometric or light obscuration system is used only as a back-up system for catalase-negative agents, which are only about 5% of the agents currently presenting problems.

EXAMPLE 2

In this example duplicate systems were used to compare the efficiency of transducer-catalase analysis and light obscuration analysis. A *Staph. aureus* strain which was resistant or insensitive to all antibiotics other than Tetracycline was chosen as a test organism. The organism was allowed to grow in broth and was used about two hours before turbidity was barely evident. At that time the cassettes were loaded and scanned (zero hour) and failed to manifest any light obscuration, but the transducer readings at this base line were 0.08 psi.

After two hours incubation at 37° C., turbidity was barely evident in the control cell, with light obscuration at 0.070; the Kanamycin cell (K), with light obscuration at 0.040; and the Streptomycin cell (S), with light obscuration at 0.050. However, the transducer readings indicated excess pressures in these three cells, with psi in excess of 1.00 and also in cells which were negative for light obscuration; the Penicillin cell (P) showed an increase from the base line of 0.08 to 0.11; Ampicillin (Am) showed an increase to 0.14; and Tetracycline (Te) a decrease to 0.04 psi. In view of the reproducibility of the transducercatalase system, the small increases and decreases in pressure have true meaning in determining the antibiotic of choice.

At four hours, the Erythromycin cell (E) became slightly turbid with light obscuration of 0.140, but the Penicillin, Ampicillin and Tetracycline cells still remained clear. However, the Penicillin cell now gave a reading of 0.19 psi, a further increase over the 2-hour reading; the Ampicillin cell showed 0.22 psi, and the Tetracycline cell showed 0.00 psi, a further decrease. Since bacterial catalase is highly labile when the bacterial cell is not biosynthetically active, this type of measurement insures reading of true bactericidal effects.

According to the light obscruation tests, there were three candidate antibiotics at the 4-hour period. Continued incubation of the light obscuration system took as long as eight or more hours before obscuration developed in the Penicillin and Ampicillin cells, whereas the transducer method of measuring catalase gave an indication of the choice antibiotic at two hours, which was confirmed at four hours.

EXAMPLE 3

In this example, a further comparison of the catalase-transducer system versus the light obscuration system was made. These comparisons were conducted in duplicate, one series made by the catalase-transducer system and the second was based on light obscuration. The time at which an antibiotic of choice could be determined by the catalase-transducer system was used as a base line. The excess time required to obtain the same results by light obscuration is illustrated in Table V below. When the catalase test indicated two to three antibiotics were bacteriostatic, the additional time required before these cells manifested light obscuration at 540 nm is set forth in Table V. Bactericidal effects were determined by the catalase method when multiple readings indicated a steady decrease in transducer readings. Bacteriostasis was determined when a steady but minimal increase in transducer readings was constant over multiple readings.

TABLE V

| Organism | Excess Time* |
| --- | --- |
| Staph. aureus | 8 hr. |
| Pseudomonas | 6 hr. |
| Proteus | 16 hr. |
| E. coli | 13 hr. |
| Klebsiella | 4 hr. |
| N. catarrhalis | 10 hr. |
| Hemophilus | 18 hr. |
| C. albicians | 8 hr. |

*Additional Time Required When Antibiotic Sensitivity Was Determined by Measuring Light Obscuration Over That Required When Antibiotic Sensitivity Was Determined by Measuring Catalase From the foregoing table it is seen that considerable periods of additional time are required to determine the sensitivity of an antibiotic by measuring light obscuration than by the catalase-transduction system. This, of course, is extremely important in determining an effective antibiotic for a patient, as indicated before, in the shortest possible period of time.

EXAMPLE 4

In this example, the consistency of quantification of catalase-transducer analysis as compared to light obscuration analysis. Ten replicate tubes were filled with broth containing E. coli at a concentration of $1 \times 10^4$ cfu/ml. This level of bacteria will barely manifest light obscuration in two hours if incubated at 37° C. The tubes were incubated at 37° C. and after two hours five tubes were read by the transducer and the other five by light obscuration. The results of this experiment are shown in Table VI below.

TABLE VI

| Tube no. | Transducer (psi) | Light Obscuration |
| --- | --- | --- |
| 1 | .25 | .060 |
| 2 | .25 | .074 |
| 3 | .24 | .069 |
| 4 | .25 | .052 |
| 5 | .25 | .064 |

The results set forth in Table VI indicate the consistency of quantification of the catalase-transducer analysis and the inconsistency of the light obscuration analysis.

EXAMPLE 5

In this example, experiments were conducted measuring bacterial multiplication as compared to catalase synthesis with E. coli as a model agent. E. coli was suspended in nutrient broth, and the broth culture was further diluted in fresh broth in order that a low catalase measurement (by transducer) was attained at zero time. The culture was then incubated at 37° C. and samples were obtained for plating and catalase assay at 20-minute intervals.

The test results showed a 50% increase in transducer reading after 20 minutes incubation, whereas the bacterial counts had not increased over the zero time base line count. At 40 minutes, the catalase value doubled, and bacterial counts only increased about 10%. After one hour, catalase value was the same as the 40 minute level, but the bacterial count had doubled, indicating that during the first 40 minutes catalase synthesis was taking place, and between 40 minutes and one hour, durimg binary fission, no additional catalase was produced.

Additional experiments with Staphylococcus aureus, Proteus and Pseudomonas gave essentially the same results. Based on this type of data, in serious cases it is feasible to select an antibiotic within 20-40 minutes that will have some effect on the pathogen. By allowing the test to proceed further with a duplicate cassette for 3-4 hours, confirmatory data will be obtained as to whether the early reading gave bactericidal or bacteriostatic information, thus allowing the physician to make a change in thereapy, if necessary, within a very short period of time.

EXAMPLE 6

This example indicates the effect of combining quaternary compounds with hydrogen peroxide. As previously mentioned, the use of catalase-transducer analysis for detecting antibiotic sensitivities causes an aerosolization of pathogenic organisms by the generation of an aerosol when the transducer needle is inserted. This aerosol must be contended with for safety purposes. Quaternary compounds were tested and found to be compatible with peroxide. Different concentrations of Roccal were added to a concentration of 10% hydrogen peroxide. Just prior to reading samples on the transducer, 1 ml peroxide with Roccal were added to the 9-ml broth culture of Staph. aureus. After fifteen minutes' incubation at 25° C., the tube was shaken and read on the transducer. The results of this test are shown in the following table, Table VII.

TABLE VII

| Final concentration of Roccal | Transducer readings (psi) | Plating |
| --- | --- | --- |
| None | 1.25, 1.29 | + + + + |
| 1:100 | 2.48, 2.50 | 0 |
| 1:1000 | 1.94, 1.90 | 0 |
| 1:10,000 | 1.45, 1.50 | + |
| 1:1000,000 | 1.27, 1.24 | + + + |
| Roccal 1:100--No $H_2O_2$ | 0.00, 0.00 | |

From the above table it is noteworthy that in the presence of Roccal, catalase titers were higher. This is apparently due to lysing of the bacteria, with exposure of additional catalases. Roccal efficiently inactivated the bacteria as indicated under "Plating". Plating of the bacteria was performed by immediately treating a sample of the culture with a cation resin to remove free quaternary compounds, and then assaying the undiluted resin supernate on agar plates. Sterility could be maintained even at a final concentration of 1:1000 Roccal. Roccal by itself (in the absence of bacterial catalase) had no effect on peroxide per se.

It is thus manifest from these results that the peroxide reactant could be contained in Roccal and, used as described above, without concern of aerosolization of pathogenic organisms. The same is true of the other quaternary compounds ser forth herein.

Experiments conducted with a broth culture of Staphylococcus aureus indicated that a number of factors play major roles in the reproducible quantification of bacterial catalase. These include (a) peroxide concentration, (b) volume of liquid to air space in the reactant tube or cell, (c) release of aqueous phase $O_2$ in the void space in the reactant tube or cell, and (d) incubation time of the reactants, that is peroxide and bacteria.

EXAMPLE 7

In this example the effects of peroxide concentration on quantification of bacterial catalase are demonstrated. Early experiments revealed that excess peroxide added to a bacterial culture denatured the catalase and the denatured enzyme was not able to act as an efficient catalyst. Therefore, a titration was conducted to determine the optimal ration between peroxide and bacterial catalase. A frest culture of *E. coli* grown in trypticase soy broth was diluted in broth so that the diluted bacterial stock manifested a transducer reading of about 0.5 psi against a final concentration of 1% peroxide. This bacterial stock was dispensed (9 ml aliquots) into multiple tubes, and representative tubes were treated with different final concentrations of peroxide. All tubes had a final volume of 10 ml. The tubes were stoppered, and after 15 minutes incubation at room temperature, were shaken and read on the transducer. The results of this test are shown on the table below.

TABLE VIII

Peroxide Titration against *E. coli*

| Final percent peroxide | Transducer readings (psi) |
|---|---|
| Control-none | −.04 |
| 0.01 | .02 |
| 0.025 | .32 |
| 0.05 | .40 |
| 0.075 | .46 |
| 0.1 | .55 |
| 0.25 | .55 |
| 0.5 | .52 |
| 0.75 | .57 |
| 1.0 | .55 |
| 1.25 | .50 |
| 1.5 | .47 |
| 1.75 | .46 |
| 2.0 | .42 |
| 2.25 | .31 |
| 2.5 | .25 |
| 2.75 | .21 |
| 3.0 | .12 |

Final concentrations of 0.1% to 2% peroxide in the final reactant product gave similar transducer values. However, less peroxide than 0.1% therein yielded lower catalase detection sensitivities. Excess peroxide (2.25% or greater) caused denaturation of the catalase as indicated by the lower transducer values. In view of these results, a final percentage of 1% by weight peroxide was selected as preferred for use in all future experiments; although 0.15% to 2.25% by weight provide acceptable results. Repeat experiments with excess bacterial catalase indicated that 1% final peroxide was an efficient level. Similarly, results with other bacteria, e.g., *Staphylococcus aureus, Proteus vulgaris,* and *Pseudomonas* gave essentially the same results as described above.

EXAMPLE 8

This example has to do with the effect of the volume of liquid and of air space. When different volumes of a heavy broth culture of bacteria were added to 15-mil Vacutainer tubes in replicates of two and the tubes were treated with a final concentration of 1.0% peroxide and incubated at 25° C. for 30 minutes, a wide variation in transducer readings was obtained. These samples were not shaken before reading on the transducer, and the results are shown in Table IX below.

TABLE IX

| Bacteria, ml | Transducer Readings |
|---|---|
| 4 | 0.2, 0.7 |
| 6 | 0.4, 0.1 |
| 8 | 1.0, 0.5 |
| 10 | 2.1, 1.6 |

There is no evidence of linearity among the different volumes of bacterial catalase added to the tubes. For example, if a 10-ml broth culture gave a transducer reading of 2.1 psi, 8 ml should have given 80% of that pressure. Thus, it was evident that the void space was affecting the results, as well as the fact that newly formed oxygen gas was not escaping into the void space.

EXAMPLE 9

This example concerns the effect of incubation time of the reactants, peroxide and bacteria. A broth culture of *Staph. aureus* was diluted in broth to contain a bacterial catalase concentration which gave a transducer reading of 5.0 psi and a second dilution was made in broth to give a lesser reading of 0.5 psi using a 30-minute incubation period prior to reading. These two stocks of bacterial catalase were then dispensed into Vacutainer tubes (9-ml volume/tube), and each sample was treated with a final of 1.0% peroxide. After stoppering, the samples were held at room temperature (25° C.), as indicated in Table X, column 1.

TABLE X

| Time (minutes) of incubation | Transducer readings (psi) | |
|---|---|---|
| | Heavy bacterial culture | Light bacterial culture |
| 0 | 0.4, 0.4 | 0.00, 0.00 |
| 2.5 | 1.5, 1.7 | 0.05, 0.02 |
| 5.0 | 2.2, 2.3 | 0.20, 0.23 |
| 10 | 4.0, 4.0 | 0.31, 0.30 |
| 15 | 4.5, 4.4 | 0.42, 0.44 |
| 20 | 4.6, 4.6 | 0.43, 0.44 |
| 25 | 4.9, 4.7 | 0.48, 0.45 |
| 30 | 4.9, 4.9 | 0.48, 0.46 |

The tubes were shaken immediately before reading on the transducer, and as shown in the above Table X, in fifteen minutes the acute slope tapers to a plateau, and very little additional catalase is measured thereafter. Thus, fifteen minutes was preferred and chosen for incubation of the reactants in all subsequent experiments.

EXAMPLE 10

This example demonstrates the effect of release of aqueous phase oxygen. It was presumed that shaking the tubes prior to reading values in the transducer might produce more reproducible and linear results. This experiment was performed using replicates of 4 tubes for each sample and the results, which are set forth in the following Table XI, confirm that premise.

TABLE XI

| Volume of bacterial suspension, ml | Transducer values in psi | |
|---|---|---|
| | No shaking of tubes | Shaking of tubes |
| 8 | 1.4, 0.9, 1.7, 1.2 | 3.0, 3.1, 3.2, 3.0 |
| 10 | 2.6, 1.9, 1.5, 2.1 | 3.5, 3.6, 3.6, 3.6 |
| 12 | 2.8, 2.0, 1.9, 2.4 | 4.1, 4.0, 4.3, 4.2 |

The results of this experiment demonstrate that by shaking the tubes vertically a few times, aqueous phase oxygen is released and reproducible assays are obtained. Thus, prior to transducer assay all tubes should be shaken.

EXAMPLE 11

In this example the effects of different broth volumes on detection of catalase were investigated. As described previously, 15-ml Vacutainer tubes filled with 10-ml final volumes were used to detect catalase. In order to determine the effects of smaller volumes of broth cultures, e.g., when using 1.5–2.0 ml cassettes, this experiment was conducted.

E. coli was used as the model agent. E. coli was added to broth, and when early growth was evident, the culture was diluted in fresh broth so that a barely detectable catalase reading was obtained. This simulated the processing of clinical samples containing excess bacteria, e.g., urinary infections, septic lesions, etc. 15-ml Vacutainer tubes were treated with 1.5 ml of this diluted broth culture and then the tubes were made up to 9 ml with fresh broth. Two-ml Vacutainer tubes were treated with 1.5 ml of this diluted broth culture and processed without adding fresh broth. The cultures were allowed to incubate at 37° C.; at various time intervals representative tubes were sampled by adding a final of 0.3% peroxide, holding for 15 minutes, shaking and assaying on the transducer. The results, shown in Table XII below, indicate that similar results are obtained in both types of tubes.

TABLE XII

| Incubation time (min) | Transducer readings | |
|---|---|---|
| | 15-ml Vacutainers | 2-ml Vacutainers |
| 0 | −.04 | −.04 |
| 30 | .00 | .00 |
| 60 | .12 | .29 |
| 120 | 1.06 | 1.05 |

EXAMPLE 12

In this experiment the efficacy of the catalase method against various strains of laboratory adapted bacteria and a variety of antibiotics was determined. This was accomplished by our catalase-transducer assay system.

Bacterial colonies were isolated and diluted in broth to a level which elicited a positive catalase sensitivity on the transducer. Nine-ml samples of this broth culture were added to multiple 15-ml Vacutainer tubes which contained 90 ug of the antibiotic indicated below. Samples were held for a time interval that indicated a rise in transducer reading of control tubes (without antibiotics) of at least 2-fold over the zero time control. The results of these tests are shown below in Table XIII for E. coli, Staph. aureus, Pseudo. aeruginosa, P. stuarti, and Shigella sonnei.

TABLE XIII

| Sample | Transducer readings (psi) | | | | |
|---|---|---|---|---|---|
| | P. stuarti | Staph. aureus | E. coli | Pseudo. aeruginosa | Shigella sonnei |
| Control at 0 min | .42 | 1.08 | .20 | 1.41 | .17 |
| Control at time test was read | .89[a] | 2.16[b] | .68[c] | 2.26[a] | .36[c] |
| Ampicillin | .72 R | 1.46 R | .60 R | ND | .32 R |
| Penicillin | .56 I | 1.57 R | .65 R | ND | .32 R |
| Tetracycline | .40 S | 1.07 S | .16 S | 1.38 S | .15 S |
| Chloromycetin | .38 S | 1.00 S | .19 S | 1.86 I | .32 R |
| Streptomycin | .43 S | 1.02 S | .21 S | 1.35 S | .23 I |
| Gentamycin | .36 S | ND | ND | 1.35 S | .17 S |
| Kanamycin | .36 S | ND | ND | 1.31 S | .25 I |
| Cephalothin | .37 S | ND | ND | ND | ND |

[a]Read at 30 min
[b]Read at 40 min
[c]Read at 90 min
R = resistant
I = insensitive
S = sensitive It is quite evident from these results, using a colony as the source of seed, that we can rapidly determine the antibiotic sensitivity of catalase-containing bacteria. Even when minimal catalase is present, such as in the case of Shigella, which gives a negative catalase colony reaction by previous conventional tests, we are able to determine catalase synthesis by our method in 150 minutes (not shown in Table).

EXAMPLE 13

The detection of bacteria in water used for drinking, pharmaceuticals, swimming pools, cooling towers, and other purposes may be accomplished by adding a sample of water to a bottle or container (25–1000 ml in volume or larger if necessary) and treating the test water with a final concentration of 0.3% peroxide. The relationship between fluid volume and void space conforms to those previously set forth. The presence of bacteria in the water or other test fluids is determined as follows.

The peroxide-treated water was allowed to stand at ambient temperature (protected from direct sunlight) for a period of 3–15 minutes (or more if desired, but not necessary). The bottle or container was shaken vigorously a few times to release the oxygen formed from the peroxide by catalase enzymes present in the bacteria which drove the oxygen from the aqueous phase into the gaseous phase. The resulting pressure was then measured. The amount of pressure was a direct indication of bacterial contamination of the test water.

EXAMPLE 14

The present invention can be used for determining small numbers of bacteria present in large volumes of test water. In Example 13 at least $10^4$ bacteria/ml must be present in 100 ml of test water before sufficient oxygen is released from the peroxide to provide sufficient pressure to be measured in the manometer. To detect smaller number of bacteria, as necessary in testing distilled water used for preparation of pharmaceuticals or for detecting bacteria in potable water systems, the bacteria must first be concentrated. If we assume that there is only one bacterium/ml in a water sample, this requires that $10^6$ ml of water should be passed through a bacteriological filter to retain the bacteria. The filter was placed within a vessel. The vessel was treated with 0.3% peroxide so that the peroxide infiltrates the filter membrane. The vessel was sealed, and the initial pressure derived from sealing the vessel was relieved by a bleeding valve. After 5 to 15 minutes, the vessel was agitated or shaken, and the port of the vessel that leads to a manometer or transducer was opened. The pressure reading of the manometer or the transducer was recorded, and related to a nomograph or standard to determine the approximate number of bacteria per ml present in the test water.

EXAMPLE 15

Cutting oils, which are water soluable, are used to lubricate cutting tools in various metal fabricating plants. During the course of their use, bacteria often grow in cutting oils. Often the odors produced by bacterial growth became noxious and the oils must be changed. By the time such noxious odors are manifested the oils have been heavily contaminated for many days. This may be dangerous to the health of persons exposed to aerosols generated by the bacteria contaminated cutting oils when in contact with cutting devices and gears. By periodic testing, such as daily, oils by the present catalase method and apparatus, the presence of bacteria can be determined before the levels reach magnitudes which are public health menaces.

In this example 100 ml of cutting oil was placed in a container and peroxide was added to yield a final concentration of about 1%. The relationship between the total fluids in the container and the void space was maintained as described previously. The container was sealed, held for fifteen minutes and then shaken vigorously for a few minutes. A lead from a transducer was then made to the cap of the container which contained a valve. The valve was opened and the psi was read on the transducer read-out. A positive pressure reading means that the oil is contaminated with bacteria, if 0.05–0.1 psi is produced, it indicates that about $10^5$ bacteria are present per 100/ml; if 1 psi about $10^6$, at 10 psi about $10^7$, etc. These indications allow the plant manager to change the oils before the growth of bacteria reaches seriously high concentrations. For example, if 0.1% of the bacteria in the oil are aerosoled each day, there is a great advantage in changing the oil when only $10^5$ bacteria are present per 100/ml as opposed to $10^8$. Thus, at $10^5$ concentration only 100 bacteria will be aerosolized for each 100 ml of oil, whereas if the growth were allowed to continue to the level of noxious odors being emitted (which usually is indicative of $10^8$ bacteria/100 ml), there would then be 100,000 bacteria being aerosolized per each 100 ml of oil.

EXAMPLE 16

Consumers who have bacteria in their drinking water systems can also monitor the quality of their water by the present catalase method. In this case, simple manometric systems are attached to the cap of the bottle which is used for water testing. A positive pressure reading would warn the consumer that a problem concerning his potable water system exists.

EXAMPLE 17

Distilled water used for pharmaceutical purposes often contains bacteria which grow therein using nitrogen from the air as a source of nitrent. Testing of this water as set forth in the foregoing examples readily determines whether or not there are undesirable amounts of bacteria in the water.

As previously mentioned, any desired method or means can be used to measure or indicate catalase which measures positive pressure, such as transducers, manometers, and where the presence of bacterial activity growth is to be indicated rather than quantitatively measured, any device which would indicate positive pressure can be used, such as balloons and other flexible rubber seals that would bulge under positive pressure.

The present invention therefore is well-suited and adapted to attain the objects and ends described and has the advantages and features mentioned as well as others inherent therein.

While presently preferred embodiments of the invention have been given for the purpose of disclosure, changes can be made therein which are within the spirit of the invention as defined by the scope of the appended claims.

What is claimed is:

1. A process for measuring bacterial growth activity by catalase reaction, comprising:

contacting in a closed cell a culture medium inoculated with body fluid containing a pathogenic organism with hydrogen peroxide, and a quaternary compound in amounts to provide from about 0.1% to about 2.25% by weight hydrogen peroxide and from about 0.1% to about 9.0% by weight quaternary compound in a catalase reaction product, the culture medium, hydrogen peroxide and quaternary compound being present in the closed cell in an amount of about 70% to about 90% of the volume thereof, holding the culture medium, hydrogen peroxide quaternary compound for a period of time sufficient to permit the catalase reaction, agitating the catalase reaction product in the closed cell thereby forcing $O_2$ released by the catalase reaction from the aqueous phase, and then measuring pressure resulting from the released $O_2$ as an indication of bacterial growth activity.

2. The process of claim 1 wherein,
the hydrogen peroxide is present in an amount of about 1% by weight,
the quaternary compound is present in an amount of about 1% by weight, and
the quaternary compound is alkyldimethylbenzyl ammonium chloride.

3. The process of claim 1 including,
also contacting the culture medium in the closed cell with dye in an amount to provide from about 0.1% to about 0.01% by weight in the final reaction product.

4. The process of claim 1 where,
the hydrogen peroxide is present in an amount of about 1% by weight,
the quaternary compound is present in an amount of about 1% by weight,
the quaternary compound is alkyldimethylbenzyl ammonium chloride, and
methylene blue is present in the closed cell in an amount of about 0.1% by weight.

5. A method of determining the sensitivity of a pathogen to an antibiotic comprising,
eluting in a closed cell an antibiotic in a culture medium inoculated with body fluid containing a pathogenic organism,
contacting the resulting culture medium with hydrogen peroxide and a quaternary compound in amounts to provide from about 0.1% to about 2.25% by weight hydrogen peroxide and from about 0.1% to about 9.0% by weight quaternary compound in the catalase reaction product,
the culture medium, hydrogen peroxide and quaternary compound being present in the closed cell in an amount of about 70% to about 90% of the volume thereof,
holding the culture medium, hydrogen peroxide and quaternary compound for a period of at least 10 minutes,
forcing $O_2$ released by the catalase reaction from the aqueous phase, and
then measuring any pressure resulting from the released $O_2$ as an indication of the sensitivity of the organism to the antibiotic.

6. The method of claim 5 where,
the hydrogen peroxide is present in an amount of about 1% by weight, and
the quaternary compound is present in an amount of about 1% by weight, and
the quaternary compound is alkyldimethylbenzylammonium chloride.

7. The method of claim 5 including,
also contacting the culture medium with dye in an amount to provide from about 0.1% to about 0.01% by weight in the final reaction product.

8. The method of claim 5 where,
the hydrogen peroxide is present in an amount of about 1% by weight,
the quaternary compound is present in an amount of about 1% by weight,
the quaternary compound is alkyldimethylbenzyl ammonium chloride, and
methylene blue is present in an amount of about 0.1% by weight.

9. A method of determining the sensitivity of pathogens to antibiotics comprising,
eluting in a plurality of separate closed cells antibiotics in a culture medium inoculated with body fluid containing a pathogenic organism,
contacting the resulting culture medium with hydrogen peroxide and a quaternary compound in amounts to provide from about 0.1% to about 2.25% by weight hydrogen peroxide and from about 0.1% to about 9.0% by weight quaternary compound in the catalase reaction produce,
the culture medium, hydrogen peroxide and quaternary compound being present in the closed cells in amounts of about 70% to about 90% of the volumes thereof,
holding the culture medium, hydrogen peroxide and quaternary compound for a period of at least 10 minutes,
forcing $O_2$ released by the catalase reaction from the aqueous phase, and
then measuring any pressure resulting from the released $O_2$ in the cells with a transducer as an indication of the sensitivity of the organism to the antibiotics.

10. The process of claim 9 where,
the hydrogen peroxide is present in an amount of about 1% by weight, and
the quaternary compound is present in an amount of about 1% by weight, and
the quaternary compound is alkyldimethylbenzyl ammonium chloride.

11. The process of claim 9 including
also contacting the culture medium with dye in an amount to provide from about 0.1% to about 0.01% by weight in the final reaction product.

12. The process of claim 9 where,
the hydrogen peroxide is present in an amount of about 1% by weight,
the quaternary compound is present in an amount of about 1% by weight,
the quaternary compound is alkyldimethylbenzyl ammonium chloride, and
methylene blue is present in an amount of about 0.1% by weight.

13. The process of claim 9 including,
contacting in at least one control cell a culture medium inoculated with the body fluid containing the pathogenic organism with hydrogen peroxide and a quaternary compound in amounts to provide from about 0.1% to about 2.25% by weight hydrogen peroxide and from about 0.1% to about 9.0% by weight quaternary compound in the catalase reaction product, and
measuring any resulting pressure with a transducer as an indication of bacterial growth activity in the control cell free of antibiotic.

14. The process of claim 13 where,
the hydrogen peroxide is present in an amount of about 1% by weight,
the quaternary compound is present in an amount of about 1% by weight, and
the quaternary compound is alkyldimethylbenzyl ammonium chloride.

15. The process of claim 13 including,
also contacting the culture medium with dye in an amount to provide from about 0.1% to about 0.01% by weight in the final reaction product.

16. The process of claim 13 where,
the hydrogen peroxide is present in an amount of about 1% by weight, the quaternary compound is present in an amount of about 1% by weight, the quaternary compound is alkyldimethylbenzyl ammonium chloride, and methylene blue is present in an amount of about 0.1% by weight.

17. A process of determining the sensitivity of pathogens to antibiotics comprising, inoculating a culture medium with body fluid containing a pathogenic organism, incubating the inoculated culture medium, contacting the incubated, inoculated culture medium in a plurality of separate closed cells with hydrogen peroxide and a quaternary compound in amounts to provide from about 0.1% to about 2.25% by weight hydrogen peroxide and from about 0.1% to about 9.0% by weight quaternary compound in the catalase reaction product, the closed cells including control cells and cells containing antibiotics, the culture medium, hydrogen peroxide and quaternary compound being present in the closed cells in an amount of about 70% to about 90% of the volume thereof, holding the culture medium, hydrogen peroxide and quaternary compound for a period of at least 10 minutes, forcing $O_2$ released by the catalase reaction from the aqueous phase, and then measuring any pressure resulting from the released $O_2$ with a transducer as an indication of the sensitivity of the organism to the antibiotic in those cells containing antiobiotics and as an indication of bacterial growth activity in the control cells.

18. The process of claim 17 where, the hydrogen peroxide is present in an amount of about 1% by weight, the quaternary compound is present in an amount of about 1% by weight, and the quaternary compound is alkyldimethylbenzyl ammonium chloride.

19. The process of claim 17 including, also contacting the culture medium with dye in an amount to provide from about 0.1% to about 0.01% by weight in the final reaction product.

20. The process of claim 17 where, the hydrogen peroxide is present in an amount of about 1% by weight, the quaternary compound is present in an amount of about 1% by weight, the quaternary compound is alkyldimethylbenzyl ammonium chloride, and methylene blue is present in an amount of about 0.1% by weight.

21. A process of determining sensitivity to antibiotics of a pathogenic organism comprising:

contacting in a closed cell formed of transparent material a culture medium inoculated with body fluid containing the pathogenic organism with hydrogen peroxide and a quaternary compound in amounts to provide from about 0.1% to about 2.25% by weight hydrogen peroxide and from about 0.1% to about 9.0% by weight quaternary compound in the catalase reaction product, the culture medium, hydrogen peroxide and quaternary compound being present in the closed cell in an amount of about 70% to about 90% of the volume thereof, holding the culture medium, hydrogen peroxide and quaternary compound for a period of at least 10 minutes, forcing $O_2$ released by the catalase reaction from the aqueous phase, then measuring any pressure resulting from the released $O_2$ with a transducer as an indication of bacterial growth activity, and measuring the light obscuration of the mixture of solution and inoculated culture medium.

22. The process of claim 21 where, the hydrogen peroxide is present in an amount of from about 1% by weight, the quaternary compound is present in an amount of about 1% by weight, and the quaternary compound is alkyldimethylbenzyl ammonium chloride.

23. The process of claim 21 including, also contacting the culture medium with dye in an amount to provide from about 0.1% to about 0.1% by weight in the final reaction product.

24. The process of claim 21 where, the hydrogen peroxide is present in an amount of about 1% by weight, the quaternary compound is present in an amount of about 1% by weight, the quaternary compound is alkyldimethylbenzyl ammonium chloride, and methylene blue is present in an amount of about 0.1% by weight.

25. Apparatus for measuring bacterial growth activity and sensitivity to antibiotics comprising, a plurality of closed cells, means operable to add a culture medium inoculated with body fluid containing a pathogenic organism and operable to dispense a solution of hydrogen peroxide and a quaternary compound to the closed cells in amounts to comprise 70% to about 90% of the volume of the closed cells, means to shake the culture medium and the solution to thereby force $O_2$ released by the catalase reaction from the aqueous phase, and a transducer operable to measure pressure of the released $O_2$ in the cells as an indication of bacterial growth activity and sensitivity to antibiotics.

26. The apparatus of claim 25 where, the cells are formed of a transparent material of optical quality, and includes a system operable to measure light obscuration in the cells.

27. The apparatus of claim 25 including, an incubator operable to incubate the inoculated cultural medium in the cells.

28. Apparatus for measuring bacterial growth activity and sensitivity to antibiotics comprising, a closed culture container for receiving a culture medium inoculated with body fluid containing a pathogenic organism, a plurality of closed cells adapted to receive antibiotics and the inoculated culture medium, dispenser means on the container operable to dispense the inoculated cultural medium into the closed cells, a second container for receiving a solution of hydrogen peroxide and quaternary compound, a second dispenser means on the second container operable to dispense the solution into the closed cells containing the inoculated culture medium, the first and second dispenser means operable to dispense the culture medium and solution in amounts of from about 70% to about 90% of the volumes of the closed cells, means to shake the culture medium and the solution to thereby force $O_2$ released by the catalase reaction from the aqeuous phase, and a transducer operable to measure pressure of the released $O_2$ in the cells as an indication of bacterial growth activity and antibiotic sensitivity.

29. The apparatus of claim 28 where, the cells are formed of transparent material of optical quality, and includes a system to measure light obscuration in the cells.

30. The apparatus of claim 28 including, an incubator operable to incubate the inoculated cultural medium in the cells.

31. A process involving measuring bacterial growth activity by catalase reaction, comprising:

contacting in a closed container a liquid susceptible of bacterial growth activity with hydrogen peroxide and a quaternary compound in amounts to provide from about 0.1% to 2.25% by weight hydrogen peroxide and from about 0.1% to about 9.0% by weight quaternary compound in the catalase reaction product, the liquid, hydrogen peroxide and quaternary compound being present in the closed container in an amount of about 70% to about 90% of the volume thereof, holding the liquid, hydrogen peroxide and quaternary compound a period of time to permit the catalase reaction, agitating the catalase reaction product in the closed container to thereby force $O_2$ released thereby from the liquid phase, and then measuring pressure resulting from the released $O_2$ as an indication of bacterial growth activity.

32. The process of claim 31 where, the hydrogen peroxide is present in the amount of about 1% by weight, and the quaternary compound is present in an amount of about 1% by weight, and the quaternary compound is alkyldimethylbenzyl ammonium chloride.

33. The process of claim 31 including, also contacting the liquid in the closed container with dye in an amount to provide from about 0.1% to about 0.01% by weight in the final catalase reaction product.

34. The processes of claims 31, 32 or 33 where, the liquid is water.

35. The processes of claims 31, 32 or 33 where, the liquid contains water.

36. The processes of claims 31, 32 or 33 where, the liquid is cutting oil.

* * * * *